United States Patent
Takagaki et al.

(10) Patent No.: US 12,270,797 B2
(45) Date of Patent: Apr. 8, 2025

(54) VOLATILE COMPONENT EVALUATION METHOD AND DEVICE USED THEREFOR

(71) Applicant: SODA AROMATIC CO., LTD., Tokyo (JP)

(72) Inventors: Hitoshi Takagaki, Noda (JP); Kenzo Kasai, Nodi (JP); Hanna Ochi, Noda (JP)

(73) Assignee: Soda Aromatic Co., Ltd., Tokyo (JP)

( * ) Notice: Subject to any disclaimer, the term of this patent is extended or adjusted under 35 U.S.C. 154(b) by 507 days.

(21) Appl. No.: 17/430,438

(22) PCT Filed: Feb. 7, 2020

(86) PCT No.: PCT/JP2020/004929
§ 371 (c)(1),
(2) Date: Aug. 12, 2021

(87) PCT Pub. No.: WO2020/166523
PCT Pub. Date: Aug. 20, 2020

(65) Prior Publication Data
US 2022/0187261 A1 Jun. 16, 2022

(30) Foreign Application Priority Data
Feb. 12, 2019 (JP) .................. 2019-023017

(51) Int. Cl.
| G01N 30/86 | (2006.01) |
| G01N 30/60 | (2006.01) |
| G01N 33/00 | (2006.01) |
| G01N 30/02 | (2006.01) |

(52) U.S. Cl.
CPC ..... *G01N 30/8675* (2013.01); *G01N 30/6052* (2013.01); *G01N 33/0009* (2013.01); *G01N 2030/025* (2013.01)

(58) Field of Classification Search
CPC .......... G01N 30/8675; G01N 30/6052; G01N 33/0009; G01N 2030/025
USPC .......................................... 73/23.2
See application file for complete search history.

(56) References Cited

FOREIGN PATENT DOCUMENTS

| JP | 2003-107067 A | 4/2003 |
| JP | 2007-163198 A | 6/2007 |
| JP | 2020098176 A | * 6/2020 |

OTHER PUBLICATIONS

Ando (Year: 2020).*
Yuriko Honma et al., "Development of GC-olfactometry by retronasal presentation," Nippon Nogeikagaku Kaishi, vol. 78, No. 6, 2004, pp. 572-574 (Abstract).

* cited by examiner

Primary Examiner — Alexander A Mercado
Assistant Examiner — Rodney T Frank
(74) Attorney, Agent, or Firm — DLA Piper LLP (US)

(57) ABSTRACT

An apparatus includes a first flow channel connected to a gas release channel of a gas chromatograph that sends at least a volatile component separated by the gas chromatograph into the mouth of an evaluator; a container that stores a non-gaseous flowable specimen having fluidity; and a second flow channel that sends the flowable specimen into the mouth.

7 Claims, 3 Drawing Sheets

VOLATILE COMPONENT EVALUATION METHOD AND DEVICE USED THEREFOR

TECHNICAL FIELD

This disclosure relates to a method for the evaluation of odors and an apparatus used therefor.

BACKGROUND

It is known that there are two types of aromas that are perceived when eating foods, namely, orthonasal ones that directly reach the nose and retronasal ones that travel through the throat during eating and drinking before reaching the nose, and that they differ significantly in terms of odor balance and perception by humans. Retronasal aromas, in particular, directly affect the perceived taste of foods and represent an important element in flavor development.

GC-olfactometry (GC-O) is generally adopted to identify trace odor components in animal- or plant-derived materials. In addition, the AEDA method and the charm analysis method are also used for GC-O based screening of characteristic odor components. Such flavor analysis techniques are described, for example, in "Utilization of Gas Chromatography and Mass Spectrometer for Flavor Analysis," Fragrance Journal, 1997-6, 12, 1997. However, there are limits to the application of these GC-O based techniques to evaluation of odor components because odor components can undergo mutual interactions such as masking and enhancement.

As a solution to the above problem with GC-O, Japanese Unexamined Patent Publication (Kokai) No. 2003-107067 proposes a method in which volatile components separated by gas chromatograph and components volatilizing from the specimen are mixed and used to perform continuous evaluation of the influence of the separated volatile components on the odor. However, it is difficult for that method to accurately predict the influence of a component existing in a liquid. It is impossible, furthermore, for that method to evaluate retronasal aromas because evaluation is made based on smelling them.

In addition, Nippon Nogeikagaku Kaishi, Vol. 78, No. 6, 2004, pp 572-574 discloses an evaluation method in which volatile components separated by gas chromatography are inhaled though the mouth rather than the nose. In that method, however, only a gaseous specimen is kept in the mouth under conditions where tastes or aromas of the test food do not exist and, therefore, there is a limit to it as a method for evaluation of retronasal aromas.

As a solution to the problems with the methods proposed in JP '067 and Nippon Nogeikagaku Kaishi, Japanese Unexamined Patent Publication (Kokai) No. 2007-163198 proposes a method of continuously mixing a volatile component separated by gas chromatograph with a liquid sample and weigh out specimens. That method allows liquid specimens to be weighed out and taken directly in the mouth for evaluation, and therefore, it is suitable for evaluation of retronasal aromas.

The method proposed in JP '198 has the disadvantage that when a plurality of components coexists in a weighed specimen, the intended component cannot be identified easily. In addition, the intervals of weighing out specimens may have to be increased to obtain them in required amounts for evaluation, but this allows the volatile components separated by gas chromatography to be mixed more easily.

SUMMARY

We thus provide (1) to (10):

(1) An apparatus having a first flow channel connected to the gas release channel of a gas chromatograph to send at least a volatile component separated by the gas chromatograph into the mouth, a container to store a non-gaseous flowable specimen having fluidity, and a second flow channel to send the flowable specimen into the mouth.

(2) An apparatus having a first flow channel connected to the gas release channel of a gas chromatograph to send at least a volatile component separated by the gas chromatograph into the mouth, a container to store a non-gaseous flowable specimen having fluidity, a second flow channel to send the flowable specimen into the mouth, a container to store an odor specimen emitting gas having an odor, and a third flow channel to send into the mouth the odor gas emitted from the odor specimen in the container.

(3) An apparatus as set forth in the paragraph (2), further having a fourth flow channel to combine the first flow channel and the third flow channel and send the volatile component and the odor gas into the mouth.

(4) An apparatus as set forth in any one of the paragraphs (1) to (3), where the discharging ends of the flow channels are combined.

(5) A volatile component evaluation method characterized in that a volatile component separated by the gas chromatograph and a flowable specimen are separately sent continuously and directly into the mouth by using an apparatus as set forth in either paragraph (1) or (4).

(6) A volatile component evaluation method characterized in that a volatile component separated by the gas chromatograph, a flowable specimen, and an odor gas are separately sent continuously and directly into the mouth by using an apparatus as set and forth in either paragraph (2) or (4).

(7) A volatile component evaluation method characterized in that a gas mixture of a volatile component separated by the gas chromatograph and an odor gas, and a flowable specimen are separately sent continuously and directly into the mouth by using an apparatus as set forth in either paragraph (3) or (4).

(8) An evaluation method as set forth in any one of the paragraphs (5) to (7), wherein the discharge flow rate of the flowable specimen is 0.5 to 10 ml per minute.

(9) An evaluation method as set forth in either paragraph (6) or (7), wherein the discharge flow rate of the odor gas is 50 to 1,500 ml per minute.

(10) An evaluation method as set forth in any one of the paragraphs (5) to (9), wherein the flowable specimen contains a gustatory component.

The use of the apparatus allowed a volatile component separated by gas chromatography and a flowable specimen to be separately sent continuously and directly into the mouth for evaluation, leading to the solution of the above problems. The volatile component evaluation method serves for simple evaluation of the influence of an odor component on the sensation during eating and drinking. It also allows an effective odor component to be identified more easily than by the conventional techniques. In addition, it serves for easy determination of the retention time of a useful component, and therefore, it serves for easy identification of that component.

Figure 1:
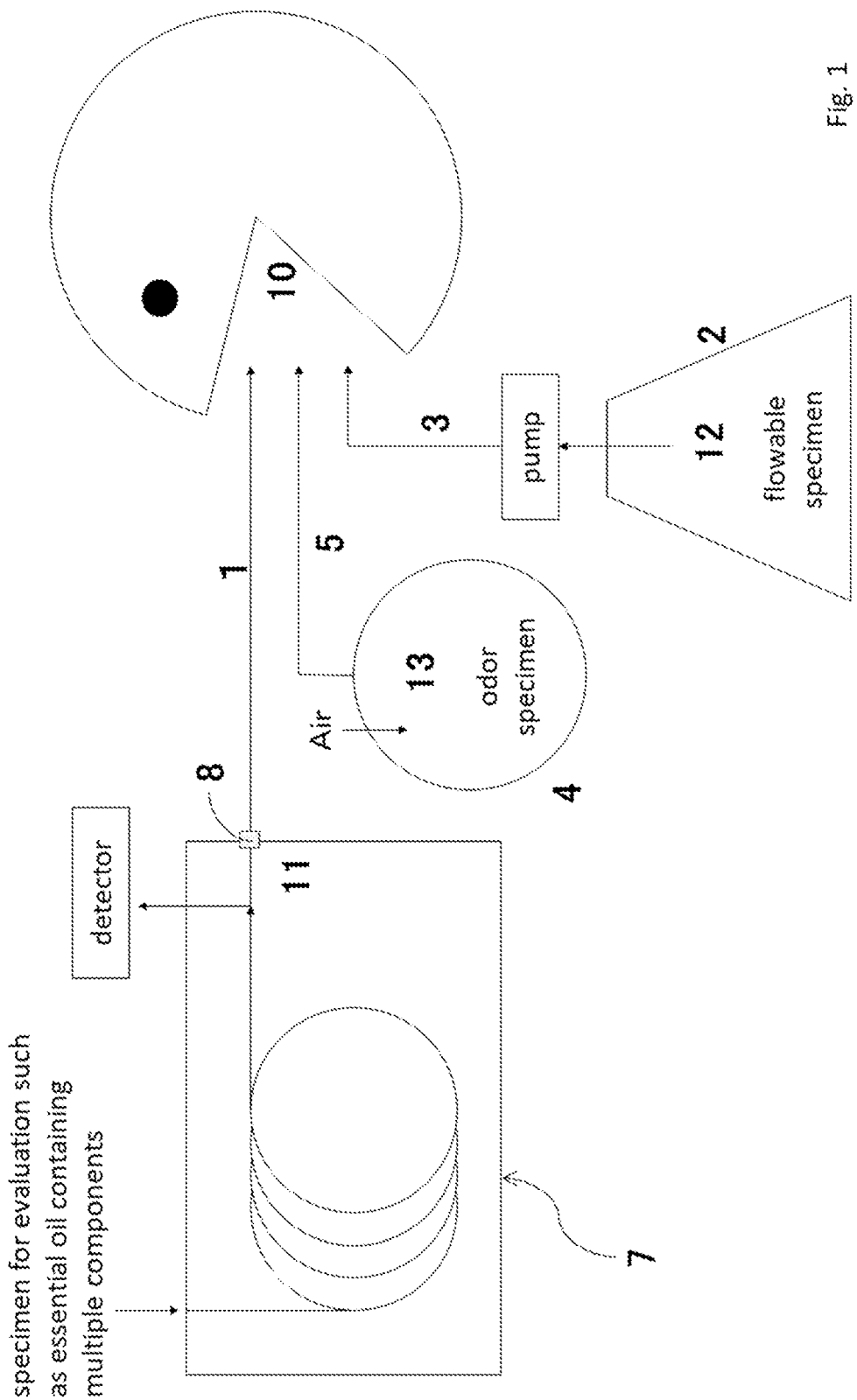
FIG. 1 is a schematic diagram illustrating the apparatus used for the evaluation method.
Figure 2:
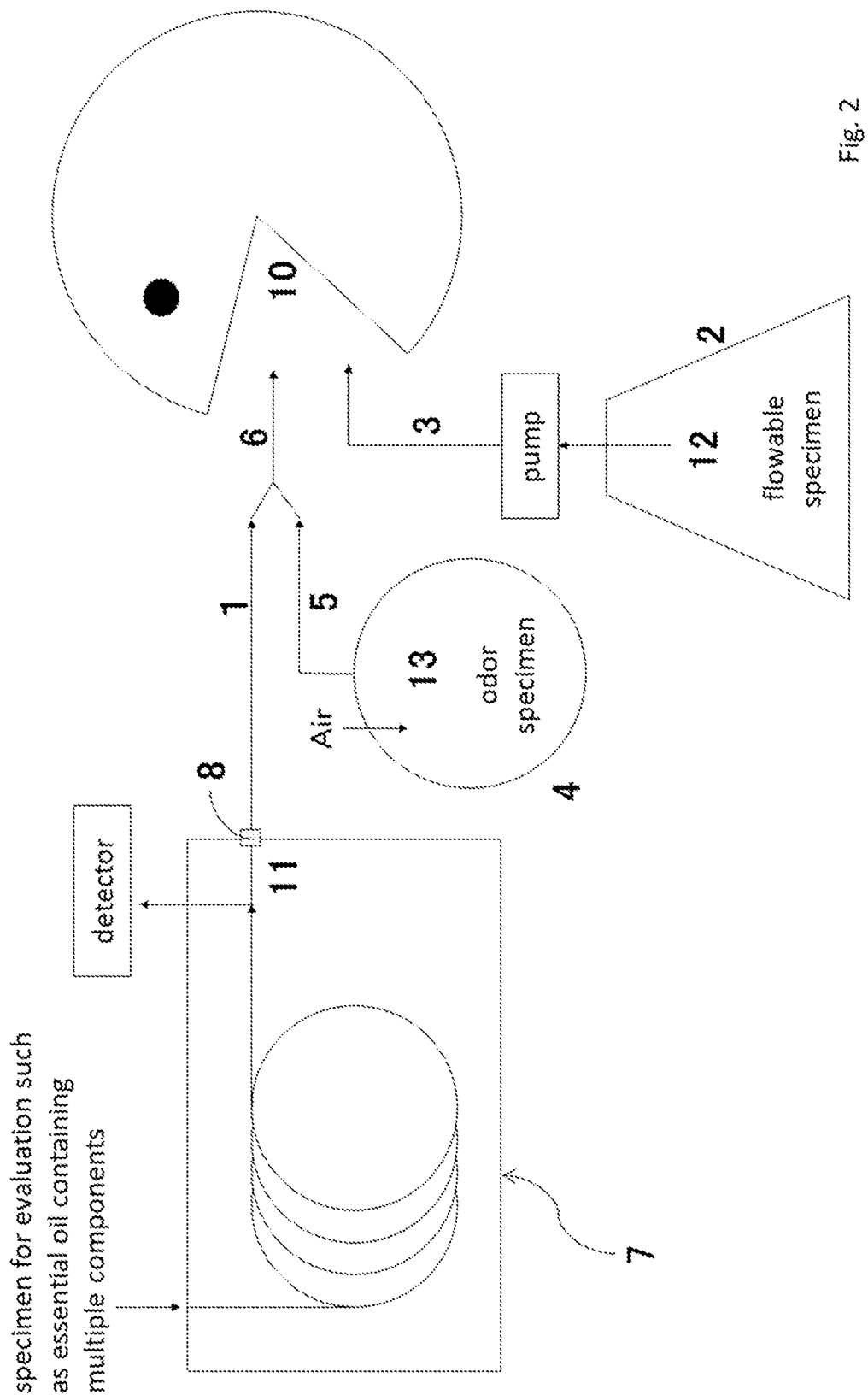
FIG. 2 depicts an apparatus having a fourth flow channel (6) which combines a first flow channel (1) and a third flow channel (5)
Figure 3:
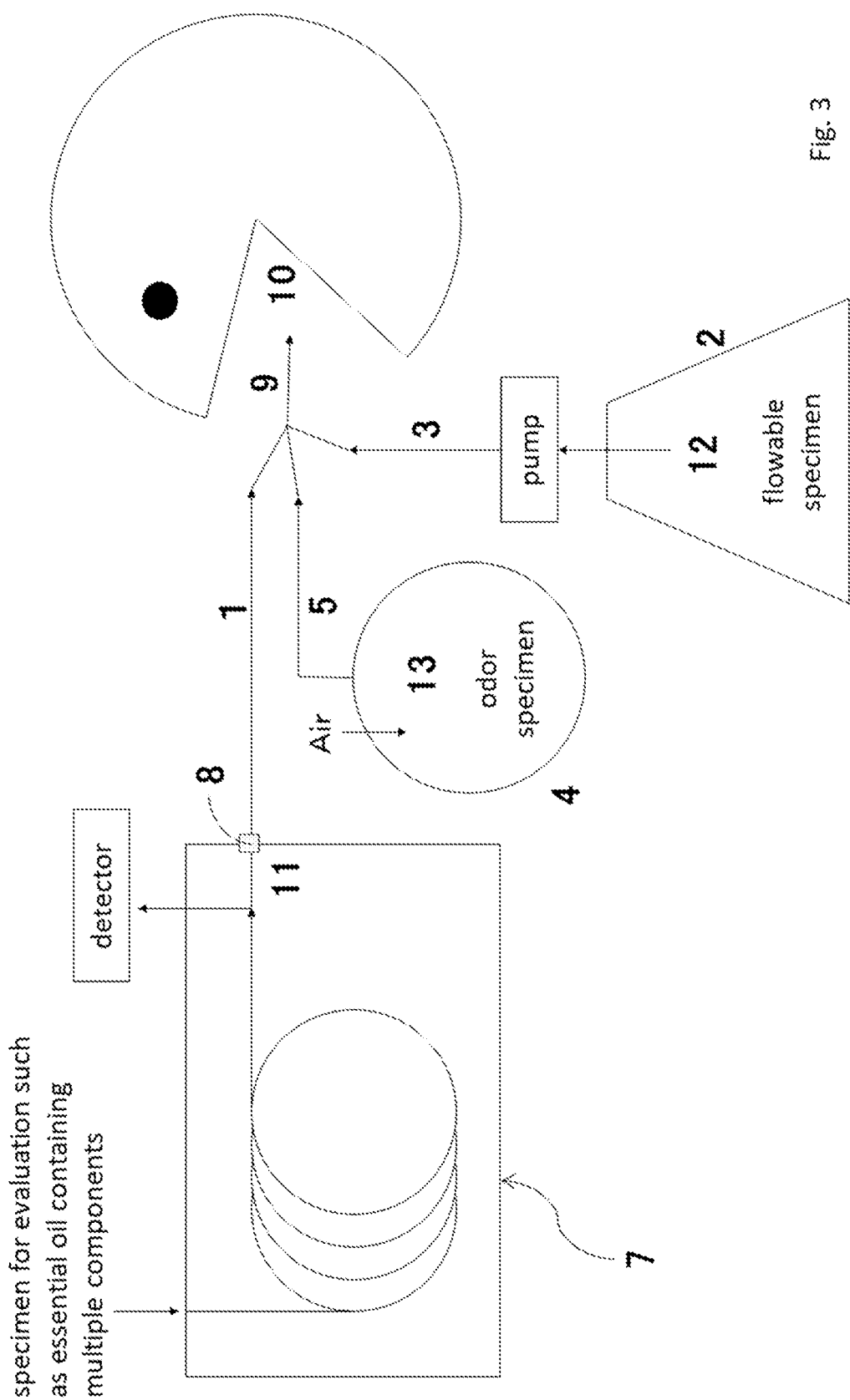
FIG. 3 depicts an apparatus having a combined flow channel (9) which combines a first flow channel (1), a second flow channel (3) and a third flow channel (5).

EXPLANATION OF NUMERALS 1. first flow channel
2. container of flowable specimen
3. second flow channel
4. container of odor specimen
5. third flow channel
6. fourth flow channel
7. gas chromatograph
8. gas release channel
9. combined flow channel
10. mouth of evaluator
11. volatile component
12. flowable specimen
13. odor specimen

DETAILED DESCRIPTION

Our apparatus is an apparatus for oral evaluation of a volatile component wherein a volatile component separated by gas chromatography (occasionally referred to as volatile component) and a non-gaseous flowable specimen having fluidity (occasionally referred to as flowable specimen) are separately sent continuously and directly into the mouth. The apparatus is roughly described below with reference to FIG. 1. The apparatus contains a first flow channel 1 connected to the gas release channel 8 of a gas chromatograph 7 to send a volatile component 11 into the mouth of an evaluator 10, a container 2 to store a flowable specimen 12, and a second flow channel 3 to send the flowable specimen 12 into the mouth of an evaluator 10. In this way, the volatile component 11 and the flowable specimen 12 can be separately sent directly into the mouth of an evaluator 10 through the flow channels.

With the aim of, for example, supplementing odor components contained in the flowable specimen, the apparatus may have, in addition to the above structure, a container 4 to store an odor specimen that emits gas having an odor (occasionally referred to as odor specimen 13) and a third flow channel 5 to supply the gas emitted from the odor specimen 13 (occasionally referred to as odor gas) in the container 4 to the mouth of an evaluator 10.

The first flow channel 1 and the third flow channel 5 may be combined to form a fourth flow channel 6. In this instance, it is preferable for the first flow channel 1 to act as the main flow to become the fourth flow channel 4. In addition, the second flow channel 3 may also be combined with these flow channels to form combined flow channel 9.

In view of, for example, the fact that the gas component containing a volatile component or the gas component containing a volatile component and an odor gas may not necessarily be dissolved completely in the flowable specimen and also that the gas component is likely to remain in the flow channel as the gas component is combined with the flowable specimen, it is more preferable for the second flow channel 3 to be an independent channel to allow the gas component and the flowable specimen are separately sent directly into the mouth. When the second flow channel 3 is combined, the flow channel after the confluence should preferably be as short as possible.

A specimen for evaluation that contains, for example, an odoriferous component, a trace odor component obtained from plant- or animal-derived material, or essential oil containing multiple components is injected in a gas chromatograph and separated into a plurality of volatile components 11. A volatile component 11 separated by gas chromatography 7 is divided into two flow channels, of which one is connected to a detector and the other acts as the first flow channel 1, and it is discharge into the mouth of an evaluator 10 from the end of the first flow channel 1. If the first flow channel 1 is too large in diameter, it will be difficult to hold it in the mouth for evaluation and the volatile component 11 may be retained in the channel. If it is too small, on the other hand, the gas is likely to be discharged strongly from the outlet to achieve a necessary flow rate, making evaluation difficult. Accordingly, it is preferable for the outside diameter to be about 0.4 to 15 mm. It is preferable for the fourth flow channel 6 to have the same diameter as the first flow channel 1. In addition, air may be supplied into the first flow channel 1 to adjust the flow rate and temperature appropriately. The air supply rate may be controlled as desired unless it hinders the evaluation work, and it is preferably about 5 to 200 ml per minute.

A flowable specimen 12 is fed to the container 2, sent into the second flow channel 3 by an appropriate method such as gravity fall and pumping, and discharged from the end of the second flow channel 3. The use of a pump is preferred because it permits simple and accurate control of the rate of flow into the second flow channel 3. The supply rate of a flowable specimen may be adjusted as desired unless it hinders the evaluation work, but it is preferably about 0.5 to 10 ml per minute. The tube used for the second flow channel 3 is preferably a material having heat resistance and acid resistance. Regarding its diameter, it will be difficult to hold it in the mouth for evaluation if it is too large in diameter whereas if it is too small in diameter, the flowable specimen is likely to be discharged strongly from the outlet to achieve a necessary flow rate, making evaluation difficult. Accordingly, it is preferable for the diameter to be about 0.4 to 15 mm to allow the linear speed to be in an appropriate range. In addition, to prevent the flowable specimen from flowing backward into the first flow channel 1 or the third flow channel 5, it is preferable for the length of the tube used for the second flow channel 3 to be adjusted so that the end of the second flow channel 3 can reach a deeper position in the mouth than the ends of the first flow channel 1 and the third flow channel 5.

Any material that at least can be fed at a constant rate by a pump and can be ingested into the human body through the mouth can be used as a flowable specimen, and examples thereof include fruit drinks, milk, beer, soup, curry sauce, coffee, Japanese shochu liquor mixed with soda water, other liqueurs, extracts, jelly drinks, carbonated drinks, and heated drinks. Drinks containing odor components or gustatory components are commonly used, but materials free of odor components and gustatory components such as water and edible oil, may be adopted as required in the evaluation of, for example, tactile sensation in the mouth. In a solid material, it may be ground or crushed and mixed with water or the like to prepare an applicable pasty specimen.

An odor specimen 13 is fed to the container 4. Odor gas emitted from the odor specimen 13 is carried continuously into the third flow channel 5 by the carrier gas injected in the container 4 and discharged from the end of the third flow channel 5. The rate of odor gas supply into the mouth may be controlled as desired unless it hinders the evaluation work, and it is preferably about 50 to 1,500 ml per minute. Regarding the gas supply tube used for the third flow channel 5, it will be difficult to hold it in the mouth for evaluation if it is too large in diameter whereas if it is too small in diameter, the gas is likely to be discharged strongly from the outlet to achieve a necessary flow rate, making evaluation difficult. Accordingly, it is preferable for the diameter to be about 0.4 to 15 mm to allow the linear speed to be in an appropriate range.

The odor specimen 13 may be in any form such as solid and liquid as long as it emits an odor gas. When the odor specimen is in a liquid, it is preferable to stir it by a generally known method in the container 4, and a device for replenishing the liquid may be provided as required. When the odor specimen is in a gaseous state, a gas collection bag or the like containing the gas may be connected to the third flow channel 5 to supply it continuously using a pump or the like.

It is preferable to combine the flow channels at the discharging ends to permit easy evaluation by the rater, and it is more preferable to use a replaceable mouthpiece to combine them. Such a mouthpiece preferably has a structure that does not impede breathing or swallowing, and the use of a tubular one is preferred. Commonly used materials for the mouthpiece include glass, silicon resin, and PTFE, and in particular, elastic ones such as silicon tube are preferred. In addition, the rater has to keep it in the mouth for a long period of time for evaluation and, therefore, it is preferable for the mouthpiece to have an outside diameter of 30 mm or less to not impose heavy strains on the rater.

To assist breathing of the rater, it is preferable to provide an air hole in any of the first flow channel 1, third flow channel 5, fourth flow channel, and mouthpiece, and it is more preferable for the mouthpiece to have such a hole.

Any specimen may be heated or cooled as required. To control the temperature of the container containing a specimen, generally known useful methods are available including the method of installing a heater on the outside of the container and the method of equipping the container with a jacket in which fluid flows to control the temperature. In addition, a device for measuring the temperature may be attached to the internal or external surface of the container, and the implementation of temperature control based on output from the measuring device is also a useful means. It is preferable for each container to be made of a material that does not emit volatile components such as odorous materials from itself and does not adsorb volatile components, and glass containers or the like are commonly used.

The aforementioned apparatus is used for the volatile component evaluation method. More specifically, a specimen for evaluation such as essential oil containing multiple components is first injected through the inlet of the gas chromatograph 7, and the volatile component separated in the column is sent into the first flow channel 1. On the other hand, a flowable specimen 12 is injected into the container 2 and sent into the second flow channel 3 by the aforementioned method. The rater holds the discharging ends of the first flow channel 1 and the second flow channel 3 directly in the mouth as the volatile component 11 and the flowable specimen 12 are separately sent into the mouth of an evaluator 10 continuously and directly. As a result, the volatile component 11 separated by gas chromatography 7 can be continuously subjected to functional evaluation under conditions that simulate the sensation during eating and drinking while at the same time, the components and their evaluation results can be checked against each other in a simple way based on the chromatogram.

When the flowable specimen 12 fails to give a required amount of an odor component in carrying out the aforementioned method, an odor specimen 13 containing odor that supplements the odor in the flowable specimen is put in the container 4, and the odor gas emitted from the odor specimen 13 is sent into the third flow channel 5 by the aforementioned method. The discharging end of this third flow channel 5 is held in the mouth of an evaluator 10 together with the discharging ends of the first flow channel 1 and the second flow channel 3 to allow evaluation to be performed while supplementing the odor in the flowable specimen. Depending on the purpose of the evaluation, the odor specimen 13 may be other than those for supplementing the odor in the flowable specimen.

EXAMPLES

Our methods and devices will be illustrated below in more detail with reference to examples, but the scope of this disclosure is not construed as being limited to these examples.

Example 1

Frozen and crushed vanilla beans were extracted with ether, and the extract obtained by solvent recovery (hereinafter referred to as vanilla odor extract) was injected into a gas chromatograph. The experiment used a 7890A gas chromatograph manufactured by Agilent Technologies, an FID detector, a polar capillary column (with a length of 30 m, inside diameter 0.53 mm, and film thickness 10 µm), and nitrogen gas as carrier gas for the gas chromatograph, and it was performed under a pressure of 110 kPa while heating from 120° C. to 250° C. at a heating rate of 2° C. per minute. The volatile component separated in the gas chromatograph was introduced into the first flow channel 1 while supplying air at a rate of 40 ml per minute. At the same time, a flowable specimen prepared by adding 8% of granulated sugar and 0.2% of a vanilla extract to milk was stored in the container 2 and introduced into the second flow channel 3 at a rate of 4.0 ml per minute using a micropump. A glass tube having an outside diameter of 11 mm and an inside diameter of 6 mm was used as the first flow channel 1, a glass Erlenmeyer flask used as the container 2, and a PTFE tube having an outside diameter of 1.4 mm and an inside diameter of 0.4 mm used as the second flow channel 3. A silicon tube having an outside diameter of 11 mm and an inside diameter of 6 mm, which was designed to serve as a mouthpiece, was attached to the end (discharging end) of each flow channel. These mouthpieces were held in the mouth, and the volatile component and the flowable specimen were introduced continuously and directly into the mouth while performing functional evaluation. Evaluation was performed by two expert panelists, and results suggested that a slight amount of a component that acts to enhance the gustatory stimulus to simulate an increased amount of the vanilla extract in the flowable specimen was detected at a retention time of 36.1 minutes.

Similar evaluation was also performed while adding an odor specimen during the above procedure to supplement the odor concentration in the flowable specimen introduced into the mouth. The odor specimen was prepared by adding 8% of granulated sugar and 1% of a vanilla extract to milk. The odor specimen was put in the container 4, which was added to the apparatus used for the method, and stirred continuously in the container while the odor gas generated from the odor specimen was carried by the carrier gas into the third flow channel 5. A glass round bottom flask was used as the container 4 and a silicon tube having an outside diameter of 11 mm an inside diameter of 6 mm was used as the third flow channel 5. The third flow channel 5 was joined to a near end portion of the first flow channel 1. Results of the evaluation clearly showed that a component that acts to enhance the gustatory stimulus to simulate an increased amount of the vanilla extract in the flowable specimen was detected at the same retention time of 36.1 minutes as above.

Although the component detected at the retention time of 36.1 minutes gave no peak in the gas chromatograph, it was identified as 3-hydroxy-4,5-dimethyl-2(5H)-furanone based on note and RI analysis.

Comparative Example 1

A comparative experiment was performed to determine whether it was possible to identify the aforementioned 3-hydroxy-4,5-dimethyl-2(5H)-furanone by the method described in JP '198. The aforementioned vanilla odor extract was injected in the gas chromatograph set up under the same conditions as in Example 1, and the volatile component separated was introduced into a gas flow channel connected to the discharge path of the gas chromatograph. At the same time, ethanol was put in a specimen container disposed outside the path of the gas chromatograph, and using a metering pump, the ethanol was introduced into a liquid flow channel designed to supply the liquid from the specimen container at a rate of 0.5 mL per minute. The outflow gas from the gas chromatograph was brought into contact with ethanol at the confluence of the gas flow channel and the liquid flow channel to provide a mixture of the volatile component separated by the gas chromatograph and ethanol. This mixture was fractionated using a fraction collector. The fraction collector was set to a sampling switchover interval of 1 minute, and a 0.5 mL portion was sampled at a time to obtain a total of 80 fractions which were numbered 1 to 80. A beverage base was prepared by adding 8% of granulated sugar and 0.2% of a vanilla extract to milk and these 80 fractions were mixed with it at a mixing ratio of 1:100 to provide 80 samples for evaluation. These evaluation samples were compared to the as-prepared beverage base by six expert panelists. Results of the evaluation showed that the evaluation samples containing the No. 38 or No. 39 fraction had a component acting to enhance the gustatory stimulus to simulate an increased amount of the vanilla extract in the beverage base.

In view of the above result, to identify the component existing in the No. 38 and No. 39 fractions and acting to enhance the gustatory stimulus to simulate an increased amount of the vanilla extract in the beverage base, the No. 38 and No. 39 fractions were subjected to GC/MS analysis and as a result, 54 components in the No. 38 fraction and 39 components in the No. 39 fraction were identified. The analysis, however, failed in identifying 3-hydroxy-4,5-dimethyl-2(5H)-furanone.

Example 2

Except for using a flowable specimen and an odor specimen prepared by adding 8% of granulated sugar and 1% of a vanilla extract to milk, the same procedure as in Example 1 was carried out to perform functional evaluation of the detected components. Furthermore, Example 2 was focused on 3-hydroxy-4,5-dimethyl-2(5H)-furanone, ethyl cinnamate, acetic acid, and guaiacol as volatile components having known detection times, and each volatile component was examined to determine how its functional evaluation results differ according to different evaluation methods. For comparison, the following evaluations were performed: a functional evaluation using a common GC for olfactometry and smelling only the volatile component separated from the gas chromatograph in the nose (Comparative Example 2), a functional evaluation using the method described in JP '067, which is the same as the method of Example 2 except for excluding the flowable specimen, and smelling only the volatile component separated from the gas chromatograph and the odor specimen in the nose (Comparative Example 3), and a functional evaluation using the same method as used in Comparative Example 3 and keeping the volatile component separated from the gas chromatograph and odor gas in the mouth (Comparative Example 4). Results of the evaluations are shown in Table 1.

TABLE 1

| Component | Example 2 | Comparative Example 2 | Comparative Example 3 | Comparative Example 4 |
|---|---|---|---|---|
| Ethyl cinnamate | Enhancing gustatory stimulus to simulate an increased amount of vanilla extract | Simulating matsutake mushroom | Emphasizing balsam-like note | Emphasizing balsam-like and sweet notes |
| 3-hydroxy-4,5-dimethyl-2(5H)-furanone | Enhancing gustatory stimulus to simulate increased amount of vanilla extract | Burnt sweetness | Emphasizing burnt sweet note | Emphasizing sweet note |
| Acetic acid | No detectable changes | Acid smell | Containing acid smell | Containing acid smell |
| Guaiacol | Emphasizing note of luxurious vanilla ice cream | Phenolic Chemical smell | Emphasizing spicy note of vanilla | Emphasizing spicy note of vanilla |

Results of the evaluations show that ethyl cinnamate simulated the matsutake mushroom when evaluated by the method described in Comparative Example 2 whereas a vanilla balsam-like note was emphasized in Comparative Examples 3 and 4. On the other hand, in Example 2, which used our method, it acted to enhance the taste impression similar to an increased amount of the vanilla extract. Furthermore, whereas acetic acid caused undesirable changes in Comparative Examples 3 and 4, no changes were detected in Example 2. In addition, whereas guaiacol emphasized the spicy note of vanilla in Comparative Examples 3 and 4, it emphasized a luxurious note of vanilla ice cream in Example 2. These results show that the use of our method serves to evaluate how different components having a vanilla odor influence vanilla-flavored beverages under conditions that simulates a meal.

INDUSTRIAL APPLICABILITY

Our evaluation method serves for continuous functional evaluation of an odor component under conditions that simulate a meal while at the same time the component and its evaluation results can be checked against each other in a simple way based on a chromatogram.

The invention claimed is:

1. An apparatus comprising:
a first flow channel connected to a gas release channel of a gas chromatograph that sends at least a volatile component separated by the gas chromatograph into the mouth of an evaluator;
a container that stores a non-gaseous flowable specimen having fluidity; and
a second flow channel that sends the flowable specimen into the mouth of an evaluator, wherein the second flow channel is separate and independent from the first flow channel, so that the volatile component and the non-gaseous flowable specimen are separate from each other at least until they exit the first flow channel and the second flow channel, respectively, such that mixing occurs for the first time, in the mouth of the evaluator.

2. A method of evaluating a volatile component wherein the volatile component separated and discharged by the gas chromatograph in the apparatus and the flowable specimen sent from the container thereof by a pump as set forth in claim 1 are separately sent continuously and directly into the mouth of an evaluator.

3. The method as set forth in claim 2, wherein the discharge flow rate of the flowable specimen is 0.5 to 10 ml per minute.

4. The method as set forth in claim 2, wherein the flowable specimen contains a gustatory component.

5. An apparatus comprising:
a first flow channel connected to a gas release channel of a gas chromatograph that sends at least a volatile component separated by the gas chromatograph into the mouth of an evaluator;
a container that stores a non-gaseous flowable specimen having fluidity;
a second flow channel that sends the flowable specimen into the mouth of an evaluator;
a container that stores an odor specimen emitting gas having an odor; and
a third flow channel that sends into the mouth of an evaluator the odor gas emitted from the odor specimen in the container, wherein each of the first flow channel, the second flow channel, and the third flow channel are separate and independent from each other, and each of the non-gaseous flowable specimen, the volatile component, and the odor gas are separate and independent of one another at least until they exit their respective flow channel, such that mixing occurs for the first time, in the mouth of the evaluator.

6. A method of evaluating a volatile component wherein the volatile component separated and discharged by the gas chromatograph in the apparatus, the flowable specimen sent from the container thereof by a pump, and an odor gas carried from the container of the odor specimen by a carrier gas as set forth in claim 5 are separately sent continuously and directly into the mouth of an evaluator.

7. The method as set forth in claim 6, wherein the discharge flow rate of the odor gas is 50 to 1,500 ml per minute.

* * * * *